United States Patent [19]

Zemel

[11] Patent Number: 4,764,464

[45] Date of Patent: Aug. 16, 1988

[54] SEMISYNTHETIC ENZYMES: APOPROTEINS FROM HEME PROTEINS AS HYDROLASES

[75] Inventor: Haya Zemel, Des Plaines, Ill.

[73] Assignee: Allied-Signal Inc., Morristown, N.J.

[21] Appl. No.: 842,086

[22] Filed: Mar. 20, 1986

[51] Int. Cl.[4] ............ C12P 7/02; C12P 7/06; C12P 7/16; C12P 7/40; C12P 7/54; C12P 7/52; C12N 9/18; C07K 13/00
[52] U.S. Cl. .................. 435/136; 435/140; 435/141; 435/155; 435/160; 435/161; 435/197; 530/385; 530/402
[58] Field of Search ............ 435/69, 72, 130, 132, 435/136, 139, 140, 141, 135, 183, 184, 188, 189, 190, 195, 196, 197; 530/385, 402, 370, 371, 379

[56] References Cited

PUBLICATIONS

Gratecos, D. and Fischer, E. H., (1974) Biochem. Biophys. Res. Commun. 58, 960–967.
R. Breslow, Science, 218, 532 (1982).
Cram, J. Am. Chem. Soc., 105, 135 (1983).
Breslow, J. Am. Chem. Soc., 103, 154 (1981).
Klotz, Proc. Natl. Acad. Sci., 68 (2), 263 (1971).

Primary Examiner—Thomas G. Wiseman
Assistant Examiner—Charles L. Patterson, Jr.
Attorney, Agent, or Firm—Thomas K. McBride; Eugene I. Snyder

[57] ABSTRACT

Proteins having a hydrophobic cavity proximate to which is a residue promoting hydrolysis of functional moieties are effective semisynthetic hydrolases. Heme proteins from which the heme has been removed usually have at least one imidazole residue proximate to the cavity, and thus act as quite effective esterases. Because the size and shape of the cavities of such proteins are capable of broad diversity a wide spectrum of substrates may be hydrolyzed by these semisynthetic enzymes.

6 Claims, No Drawings

SEMISYNTHETIC ENZYMES: APOPROTEINS FROM HEME PROTEINS AS HYDROLASES

BACKGROUND OF THE INVENTION

It has long been known that enzymes are catalysts par excellence. Not only do enzymes vastly increase the reaction rate over that of the uncatalyzed counterpart, but enzymes generally show a very high selectivity both in the transformation catalyzed and in the substrate acted upon. Thus, a relatively small structural change may convert a compound from an enzyme substrate, i.e., a material in which a particular transformation is catalyzed by an enzyme, to a nonsubstrate, i.e., material in which the same transformation is not substantially affected by the same enzyme. The high selectivity manifested by enzymes is not limited only to gross structural changes in the substrate but also to much more subtle differences such as the "handedness," or chirality, of the substrate or product being formed. Being chiral molecules themselves, enzymes generally readily distinguish between enantiomeric substrates, often showing vast differential rate constants for the reaction catalyzed and/or in the formation of enantiomeric products. Additionally, enzymes as catalysts often are remarkably selective with respect to reaction conditions, such as pH, and are effective at or near room temperature. Given these attributes, it is understandable that the preparation of synthetic enzymes has been a continuing goal of chemists and biochemists.

However desirable may be the preparation of synthetic enzymes its achievement has remained largely a dream rather than a reality. This situation undoubtedly arises from the sheer magnitude of the problem. But as the mechanisms of enzymatic reactions have been clarified, as the structures of enzymes have been elucidated, and as the relation between structure, rate, and selectivity has yielded to understanding, the nebulous outlines of solutions to the general problem of synthetic enzyme preparation have been increasingly better defined. Efforts to prepare synthetic enzymes are based on the recognition that enzymatic activity is associated with a three-dimensional structure providing a cavity which binds a substrate in proximity to a moiety which interacts strongly with a particular portion of the substrate. Thus, prior efforts may be classified broadly as being directed either toward providing a cavity which strongly and/or selectively binds substrates, or placing a reactive moiety in the necessary spatial proximity to the substrate site being transformed. Exemplifying the former approach is the use of cyclodextrins as hydrophobic cavities which extract from aqueous solutions those organic molecules having the correct shape. See, e.g., R. Breslow, *Science*, 218, 532 (1982). Exemplifying the second approach is the "remote functionalization" approach where a template in a molecule controls the site of reaction. Idem., ibid.

Most efforts directed toward constructing enzyme mimics have concentrated on hydrolases, and more particularly esterases. Hydrolases may be broadly defined as molecules which catalyze the hydrolysis of such functional groups as esters, amides, imides, imines, and so forth, whereas esterases are a subgroup which catalyze the hydrolysis of esters. Molecules with a good binding cavity based on macrocyclic structures and providing high rate accelerations have been studied by Cram, *J. Am. Chem. Soc.*, 105, 135 (1983) and by Breslow, *J. Am. Chem. Soc.*, 103, 154 (1981) as esterases. However, the mechanism of ester hydrolysis involves transfer of the acyl group from the ester to the esterase, and in the aforementioned studies the acyl group remains covalently bound to the esterase precluding further catalysis. Stated differently, the esterases of Cram and Breslow remain permanently acylated and no turnover is possible. Consequently, such esterases are in a real sense not catalysts, since they are permanently transformed during the reaction. Polyethylenimines with attached imidazole groups have been shown by Klotz, *Proc. Natl. Acad. Sci.*, 68 (2), 263 (1971) to catalyze ester hydrolysis with turnover for some substrates but the rate enhancement and binding capability are only moderate.

The reaction mechanism of esterases, as representative of hydrolases, can be generally depicted as follows.

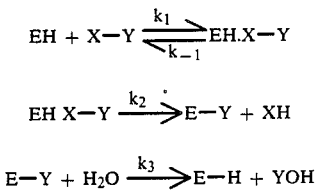

The first stage is a very fast equilibrium binding of the substrate X-Y to the enzyme EH, generally through a hydrophobic cavity, characterized by an equilibrium constant $1/K_s = k_1/k_{-1}$, usually called the binding constant. Its reciprocal, $K_s$, is the dissociation constant of the bound substrate. The second stage is the transfer of an acyl group of the substrate ester to the enzyme with concommitant production of an alcohol, XH, in a reaction whose rate constant is $k_2$. The third and last stage is the hydrolysis of the acylated enzyme characterized by the rate constant $k_3$. Usually, $k_1, k_{-1} \gg k_2, k_3$. Turnover, i.e., regeneration of free enzyme, is determined by the slower of $k_2, k_3$. If $k_3$ is much less than $k_2$ then $k_3$ is the rate of turnover, the compound EH is not regenerated in the time frame of substrate hydrolysis, and "enzyme" concentration changes during hydrolysis, which is a departure from the conventional concept of a "catalyst." Conversely, if $k_3$ is much greater than $k_2$ (high turnover) the compound EH is regenerated far more rapidly than it is acylated, and the rate of turnover is determined by $k_2$. Finally, the quantity $k_2/K_M$, where $K_M = (k_{-1} + k_2)/k_1 = K_s + k_2/k_1$, is usually referred to as the catalytic constant.

Whereas the prior efforts referred to above have afforded systems either with (1) low turnover or (2) low binding ability and rate enhancement, the claims herein are based on the discovery that a very large class of molecules, many readily derivable from naturally occurring proteins, have a cavity manifesting good binding propensity with organic substrates and which further have active residues which promote or assist hydrolysis, especially of esters. Such molecules exhibit high turnover with many substrates, and because there is such a large class of such enzyme-like molecules (referred to herein as semisynthetic enzymes), there is a good probability of finding a semisynthetic enzyme-substrate pair in which the system is truly catalytic. One large class of semisynthetic enzymes of this invention are heme proteins from which the heme portion has been removed.

SUMMARY OF THE INVENTION

The purpose of this invention is to provide a method of catalytically hydrolyzing organic compounds in aqueous solution using semisynthetic enzymes, or hydrolases. In one embodiment the semisynthetic enzyme is a heme protein from which the heme has been removed. In a more specific embodiment the hydrolase is apomyoglobin. In another embodiment the organic compounds are esters. In a still more specific embodiment the esters are linear alkyl esters of alkyl, aryl, or aralkyl carboxylic acids. Other embodiments will become apparent from the following description.

DESCRIPTION OF THE INVENTION

The construction of molecules with enzyme-like properties conceptually is simple, for such molecules need only (1) bind to the substrate, (2) promote the reaction of the bound subtrate, and (3) release the reaction products so that the "enzyme" becomes available for binding to additional substrate. Those skilled in the art of synthetic enzymes appreciate the enormous gulf between the simplicity of this mental construct and the enormous complexity and unpredictability of experimental reality. My invention is a method of catalyzing the hydrolysis of several types of organic compounds using as a catalyst an enzyme-like molecule which is a protein having a hydrophobic cavity which selectively binds to the organic compound being hydrolyzed and having proximate to the surface of the cavity a moiety which promotes or assists hydrolysis of the organic compound. An important discovery which makes this invention possible is that apoproteins whose parent is a heme protein form a large class of hydrolases which are capable of acting on several kinds of substrates, and which are especially effective as esterases. The semisynthetic enzymes of this invention act as hydrolases, i.e., they catalyze the hydrolysis of a variety of functional groups including esters.

The hydrophobic cavity acts to bind the substrate, preferably more selectively than it binds any of the reaction products. Such selectivity arises when the reaction products are more polar than the reactants, which is usually the case in the hydrolytic reactions being addressed. Preferential binding of substrate is also important to minimize product inhibition. The size and shape of the cavity will determine what substrates may be acted upon, for it should be clear that for a substrate to be effectively bound within the cavity there needs to be a good geometric fit between the cavity and the substrate. The size and shape of the cavity may be readily determined by molecular modeling for proteins with a known crystal structure, and a protein with a cavity of appropriate size and shape may be chosen with the desired substrate in mind as a way of optimizing the catalytic system.

Proximate to the surface of the hydrophobic cavity there must be at least one residue which assists or promotes the hydrolysis being catalyzed. The premier example of such a residue is the imidazole group, although serine and cysteine residues also are effective in promoting hydrolysis. It is necessary that the residue be proximate to the surface of the cavity so that it can chemically interact with the substrate which is bound within the cavity. Stated differently, if the residue is not proximate to the surface of the cavity it will be unable to chemically interact with a substrate bound within the cavity, and no catalysis will be possible.

In general, any protein bearing a prosthetic group which can be removed will afford a protein with a hydrophobic cavity, and all such proteins containing a residue which promotes hydrolysis may be used in the practice of this invention. Heme proteins from which the heme has been removed are prime examples of proteins with hydrophobic cavities which are suitable for use in this invention, for most heme proteins also have at least one imidazole residue at or near the surface of the cavity. The enzymatic or non-enzymatic heme protein may be an oxygen carrier, such as hemoglobin and myoglobin; an oxidase, as exemplified by catalase and peroxidase proteins; and cytochromes of type A(a), B(b) and other specialized cytochromes except for the C-type cytochromes. Both prokaryotic and eukaryotic cells can be used as sources for heme proteins. Some specific examples of heme proteins which may be used in the practice of this invention include hemoglobin from fish, mammals or plants (leghemoglobin), horseradish peroxidase from horseradish roots, lactoperoxidase from milk, chloroperoxidase from caldariomyces fumago, cytochrome C peroxidase from yeast, cytochrome b from *E. coli*, and cytochrome p450 from other bacteria. The heme proteins above are only illustrative of those which may be used in the practice of this invention, and when used herein "heme protein" is a generic term intended to encompass all such materials. Additional examples of heme proteins may be found in such references as "The Enzymes," J. B. Summer and K. Myrback, Editors, V. II, Part 1, 357–427, Academic Press Inc., N.Y. (1951); "Hemes and Hemoproteins," B. Chance, R. W. Estabrook, and T. Yonetani, Editors, Academic Press Inc., N.Y. (1966).

The apoprotein, i.e., a protein without its prosthetic group, is prepared by denaturing the protein, removing the prosthetic group, and then renaturing the protein. For heme proteins, the native heme may be removed by such methods as the acid-acetone method (A. Rossi-Fanelli, E. Antonini, and A. Caputo, *Biochim. Biophys. Acta*, 30, 608 (1958)); D. M. Scholler, M-Y R. Wang, and B. M. Hoffman, *Methods in Enzymology LII, Part C* (1978)) or by the acid-butanone method (F. W. J. Teale, *Biochim. Biophys. Acta*, 35, 298 (1959)). In both methods the protein is denatured, the heme is extracted into the organic phase, and the apoprotein is then renatured in aqueous solution. In its renatured form the protein preserves its tertiary and quaternary structure including the cavity, but in the absence of the heme it has lost its original functional capability.

The substrates which are used in the practice of this invention are organic molecules with at least one hydrolyzable functional moiety. Examples of such moieties include esters, thioesters, amides, imidates, and imines. Where the catalyst is an apoprotein derived from a heme protein the semisynthetic enzyme is a good esterase. Such semisynthetic enzymes also may catalyze the hydrolysis of amides, carbamates, imidates, and imines but not necessarily with equivalent results. It also needs to be emphasized that reference to "esters" also include thioesters, whether it is the acyl or alkyl oxygen, or both, which is substituted by sulfur. The esters whose hydrolysis may be catalyzed by the semisynthetic enzymes of this invention include those of carboxylic acids, sulfonic acids, phosphoric acids, phosphorous acids, and the analogous thio acids, where carboxylic and thiocarboxylic acid esters are especially desirable substrates.

Using carboxylic esters, A-CO$_2$Z, as representative of the substrates which may be used, at least one of the carboxyl or alcohol portions must be hydrophobic, i.e., either A or Z must be hydrophobic structures. This is necessary for the substrate to bind to the hydrophobic cavity. The substrate also must be of the size and shape to bind within the cavity. For example, where the cavity is long and narrow, linear (unbranched) alkyl groups are preferred for either A or Z. So, for example, where the semisynthetic enzyme is the apoprotein from sperm whale myoglobin, and where the substrates are p-nitrophenyl esters of unbranched alkyl carboxylic acids, it appears that a C10 residue is about the maximum that can fit into the cavity, and it is found that there is a rate enhancement as the alkyl chain is lengthened through C6 with no further enhancement observed thereafter.

On the other hand, where, for example, the cavity is globular a branched chain structure for A or Z may be accommodated. In fact, it may be necessary to experiment somewhat to optimize the catalyst-substrate system, but such experimentation is greatly aided by molecular modeling. Clearly, if the results of such modeling indicate that the substrate cannot be accommodated within the cavity so as to place the hydrolyzable moiety accessible to the reaction promoting residue then either a different semisynthetic enzyme needs to be used or the substrate needs to be somewhat modified.

As stated previously, the substrate should be preferentially bound to minimize product inhibition. Since the cavity is hydrophobic this implies that the product should be more polar than the reactants. Normally this is the case in ester hydrolysis, but it is a factor which needs to be kept in mind in the practice of this invention.

For this invention to be practiced the substrate must be water-soluble since the reactions are performed in an aqueous system. A water-miscible organic solvent may be used, although the amount of such organic solvents may need to be limited since they tend to denature the apoproteins which act as the semisynthetic enzymes. A common upper limit is 15% by volume, although no more than 10% is commonly employed and no more than 5% is often preferred. But it needs to be emphasized that the upper limit will be determined exclusively by the tendency of the protein to denature. Examples of solvents which may be used include the lower aliphatic alcohols, such as methanol, ethanol, n-propanol, i-propanol, polyhydric alcohols such as ethylene glycol, propylene glycol, 2-methyl-2,4-pentanediol, glycerol, and so forth, water-soluble ethers such as tetrahydrofuran and dioxane, as well as such compounds as N-methylacetamide, dimethylformamide, acetonitrile, dimethylsulfoxide, and hexamethylphosphoramide. It needs to be understood that such solvents are only illustrative of the water-miscible organic solvents that may be used in this invention, and such materials are sufficiently well known to one skilled in the art that an extensive listing is unnecessary.

The following description is generally applicable to carrying out this invention. However, it cannot be emphasized too strongly that reaction conditions are largely determined by the stability of the apoprotein. Consequently, although the description here may be applicable to some members of the class of semisynthetic enzymes used here the description should not be taken too literally.

Briefly, an aqueous solution of the organic molecule is hydrolyzed, i.e, reacted with water, in a solution containing the hydrolase. The concentration of the substrate is usually limited by its solubility, but it is advantageous to use as high a substrate concentration as is possible without encountering serious product inhibition to maximize the amount of product formation per unit reaction time. The use of water-miscible organic solvents to increase solubility is occasionally employed so long as such a solvent system does not denature the semisynthetic enzyme.

The upper concentration of the apoprotein is limited by its stability, i.e., its denaturation rate often increases with increasing concentration. For example, a concentration up to about $5 \times 10^{-4}$ molar appears to be satisfactory where apomyoglobin is used in the practice of this invention. A higher or lower concentration may be dictated by apoprotein stability under the reaction conditions in the presence of both reactants and products. The lower concentration is dictated by the necessity of having the semisynthetic enzyme present in an amount effective to catalyze the hydrolysis of the substrate. Catalysis may be effective at a concentration as low as about $10^{-7}$ molar, although the variables of substrate structure, temperature, pH, etc. make a stated lower limit quite tenuous.

The reaction temperature also is dictated by stability of the semisynthetic enzyme. When apoprotein derived from, e.g., sperm whale myoglobin is used, it often is denatured substantially at a temperature in excess of about 40° C., and consequently its use is recommended at a temperature under about 40° C. However, it needs to be emphasized that even where the semisynthetic enzyme is denatured at a higher temperature it can be used so long as its denaturation is slower than hydrolysis, although no reuse may be possible.

Finally, the pH at which the hydrolysis is performed also is dictated by the denaturation properties of the semisynthetic enzyme. For example, where the apoprotein is derived from sperm whale myoglobin a pH range between about 6.5 and about 9 is found to cause little if any denaturation.

The following examples merely illustrate this invention and are not intended to limit it in any way thereby.

EXAMPLES

The following descriptions are representative of the methods, techniques, and results used in the practice of this invention. Such a description is not, and is not intended to be, exclusive and the skilled artisan will readily recognize and appreciate the plethora of equivalents which may be substituted.

Preparation of Apomylglobin. The heme group was removed from sperm whale metmyoglobin by the acid acetone method of Rossi-Fanelli and coworkers, op. cit., from a commercially available sample which was not purified prior to use.

Hydrolysis of p-Nitrophenyl Alkanoates. The experimental methods used in the hydrolysis of these esters is exemplified by the hydrolysis of p-nitrophenyl caproate. Kinetic runs were performed with the semisynthetic enzyme, apomyoglobin, in excess of the substrate. All hydrolyses were done in 99.9% aqueous media at 25° C. at pH 8 using 0.05 molar tris(hydroxymethyl)aminomethane(TRIS) as a buffer. Each sample cuvette containing varying concentrations of apomyoglobin ($E_o$) in 1 ml of 0.05M buffer was allowed to equilibrate at 25° C. in a thermostated cell holder of a spectrophotometer. To this was added 1 microliter of $1.13 \times 10^{-2}$M p-nitrophenyl caproate in ethanol and the contents thereafter were mixed well. The increase in absorbance at 400 nm arising from the p-nitrophenolate ion was monitored as a function of time until hydrolysis was complete. The kinetic curves obtained with all enzyme concentrations exhibited first order behavior and the rate constants were calculated therefrom. Results are summarized in the following Table 1.

TABLE 1

| $E_o$ ($10^{-5}$ M) | $k_{obs}$ ($10^{-2}$ sec$^{-1}$) |
|---|---|
| 2.11 | 1.08 |
| 4.23 | 1.84 |
| 6.35 | 2.21 |
| 8.46 | 2.63 |
| 10.6 | 2.83 |

When the observed rate constants, $k_{obs}$ were plotted according to the Lineweaver Burk formulation, $$\frac{1}{k_{obs}} = \frac{K_M}{k_2} \times \frac{1}{E_o} + \frac{1}{k_2}$$

a linear relationship was obtained with $K_M = 7.4 \times 10^{-5}$M and $k_2 = 4.93 \times 10^{-2}$ sec$^{-1}$. In the absence of apomyoglobin the hydrolysis of a solution of $1.13 \times 10^{-5}$M of the same ester under the same conditions proceeded with the rate constant of $2.7 \times 10^{-5}$ sec$^{-1}$. The enhancement achieved with the semisynthetic enzyme is therefore 1800.

Turnover was demonstrated by comparing the rate of hydrolysis of a $1 \times 10^{-5}$M solution of p-nitrophenyl acetate by $5 \times 10^{-5}$M apomyoglobin to the hydrolysis rate of $1 \times 10^{-5}$M ester in the presence of a mixture of $5 \times 10^{-5}$M apomyoglobin and $5 \times 10^{-5}$M ester which was first allowed to react to 95% completion. Both rates were identical, verifying that in this case acylation rather than deacylation is the rate determining step, or $k_3$ is much greater than $k_2$. Where the same type of experiment yielded a decrease in catalysis rate in those instances the deacylation may become rate limiting. Some results of ester hydrolysis catalyzed by apomyoglobin are summarized in Table 2, where $k_2/k_M$ is often referred to as the "catalytic constant," and $k_{un}$ is the hydrolytic rate constant in the absence of apomyoglobin.

ESTER HYDROLYSIS BY APOMYOGLOBIN

| p-Nitrophenyl Ester | $K_2$(sec$^{-1}$) | $K_M$(M) | $k_2/K_M$(M$^{-1}$sec$^{-1}$) | $k_2/K_{un}$ | Turnover |
|---|---|---|---|---|---|
| Acetate | $5.8 \times 10^{-3}$ | $4.3 \times 10^{-4}$ | 13.5 | 134 | $k_3 > k_2$ |
| Propionate | $1.6 \times 10^{-3}$ | $2.5 \times 10^{-4}$ | 6.4 | 42 | $k_3 > k_2$ |
| Butyrate | $3.8 \times 10^{-3}$ | $1.43 \times 10^{-4}$ | 26.4 | 127 | $k_3 \leq k_2$ |
| Caproate | $4.93 \times 10^{-2}$ | $7.4 \times 10^{-5}$ | 67 | 1800 | $k_3 < k_2$ |
| Caprate | $3.0 \times 10^{-2}$ | $6.1 \times 10^{-5}$ | 49 | 4600 | $k_3 < k_2$ |

To ascertain that our remarkable catalytic rates result from the active site only of the empty heme pocket or cavity the following experiments were performed. In the first experiment reconstituted myoglobin was prepared from apomyoglobin and hemin, and the hydrolysis of p-nitrophenyl caproate was determined as previously described. It was found that the hydrolysis rate was not more than twice that of the spontaneous (uncatalyzed) rate. This eliminates the possibility that periperal lysine and histidine residues catalyze hydrolysis. In the second experiment the rate of hydrolysis of a solution of p-nitrophenyl acetate in buffer containing apomyoglobin, prepared as described above, was compared with the rate of hydrolysis in a similar solution which was also 8 molar in urea to ensure denaturation of apomyoglobin. After 150 seconds the reaction was 98% complete in the first solution, but only 2% complete in the urea-containing solution. This shows that the denatured protein is catalytically ineffective. These results establish the heme cavity as the active site of the semisynthetic esterase.

What is claimed is:

1. A method of hydrolyzing a carboxylic ester comprising reacting a solution of said ester with water in the presence of an apoprotein whose parent is a heme protein which is myoglobin or hemoglobin in an amount effective to catalyze the hydrolysis of the ester.

2. The method of claim 1 where the solution of the organic molecule contains a water-miscible organic cosolvent.

3. The method of claim 2 where the organic solvent is present up to about 15% by volume.

4. The method of claim 2 where the water-miscible organic solvent is selected from the group consisting of acetonitrile, dioxane, lower aliphatic alcohols, n-methylacetamide, dimethylformamide, dimethyl sulfoxide, tetrahydrofuran, hexamethylphosphoramide, ethylene glycol, propylene glycol, and glycerol.

5. The method of claim 1 where the heme protein is a hemoglobin.

6. The method of claim 1 where the heme protein is a myoglobin.

* * * * *